US00PP24383P3

(12) United States Plant Patent
Harris

(10) Patent No.: US PP24,383 P3
(45) Date of Patent: Apr. 15, 2014

(54) AZALEA PLANT NAMED 'MNIHAR027'

(50) Latin Name: ***Rhododendron* sp.**
Varietal Denomination: MNIHAR027

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 50 days.

(21) Appl. No.: 13/573,111

(22) Filed: Aug. 22, 2012

(65) Prior Publication Data

US 2014/0059727 P1 Feb. 27, 2014

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, single red flowers, easily propagated by semi-hardwood cuttings in late spring through summer, moderate growth rate under normal fertilization and moisture conditions; low growing, spreading, freely branching growth habit; grows well in containers, thrives in shade or sun and is hardy to Zone 6, is disclosed.

2 Drawing Sheets

Genus and species: *Rhododendron* sp.
Variety denomination: 'MNIHAR027'.

BACKGROUND OF THE NEW PLANT

The present invention is a new and distinct variety of evergreen azalea in the genus *Rhododendron*. This new azalea, hereinafter referred to as 'MNIHAR027', originated from a planned cross hybridization in 2001 between the female azalea plant named 'N1XE', ((unpatented cross of N1 (unpatented) and 'Conleb' (U.S. Plant Pat. No. 10,581)) and the male azalea plant named 'September Morn' (unpatented) in a controlled environment in Lawrenceville, Ga. The present invention has a blooming period of mid April and late July until frost. 'MNIHAR027' has a low growing, spreading, freely branching growth habit, and cold hardiness.

The new plant was first propagated via semi-hardwood cuttings in 2005 in Dearing, Ga. and has been asexually reproduced repeatedly by semi-hardwood cuttings in Dearing, Ga. for over 5 years, four generations. 'MNIHAR027' has been found to retain its distinctive characteristics through successive asexual propagations via semi-hardwood cuttings.

Plant Breeder's Rights for this variety have not been applied for. 'MNIHAR027' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red colored flowers;
3. Numerous single flowers;
4. Easily propagated by semi-hardwood cuttings in late spring through summer;

5. Moderate growth rate under normal fertilization and moisture conditions;
6. Low growing, spreading, freely branching growth habit;
7. Grows well in containers;
8. Thrives in shade or sun; and
9. Hardy to Zone 6.

DESCRIPTION OF THE PHOTOGRAPHS

This new azalea hybrid variety is illustrated by the accompanying photographs. The colors shown are as true as can be reasonably obtained by conventional photographic means. The photographs are of four-year-old plants grown in filtered shade and full sun in 2009 and 2011 in Dearing, Ga.

Figure 1:
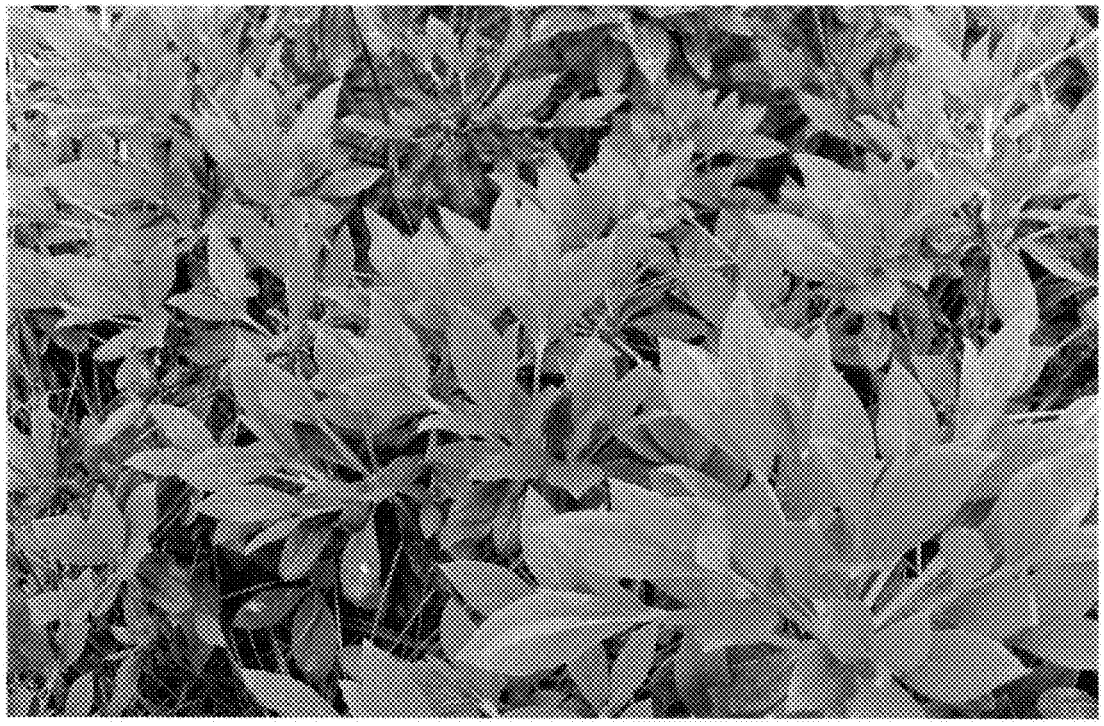
Figure 2:
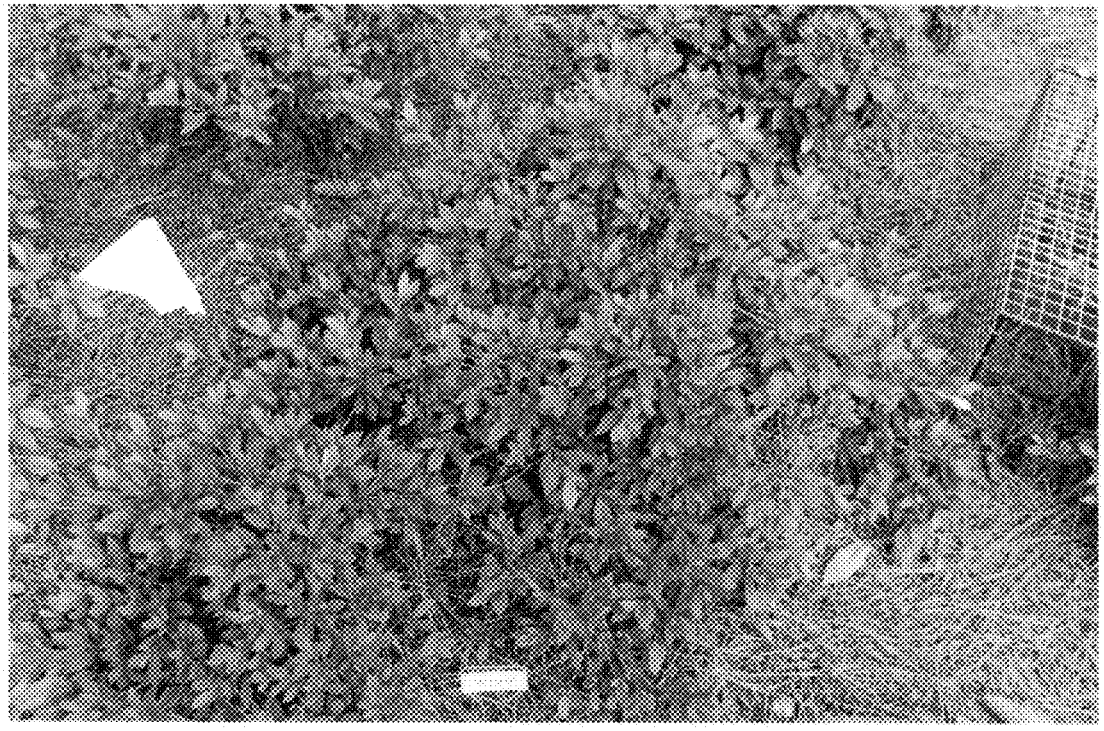
Figure 3:
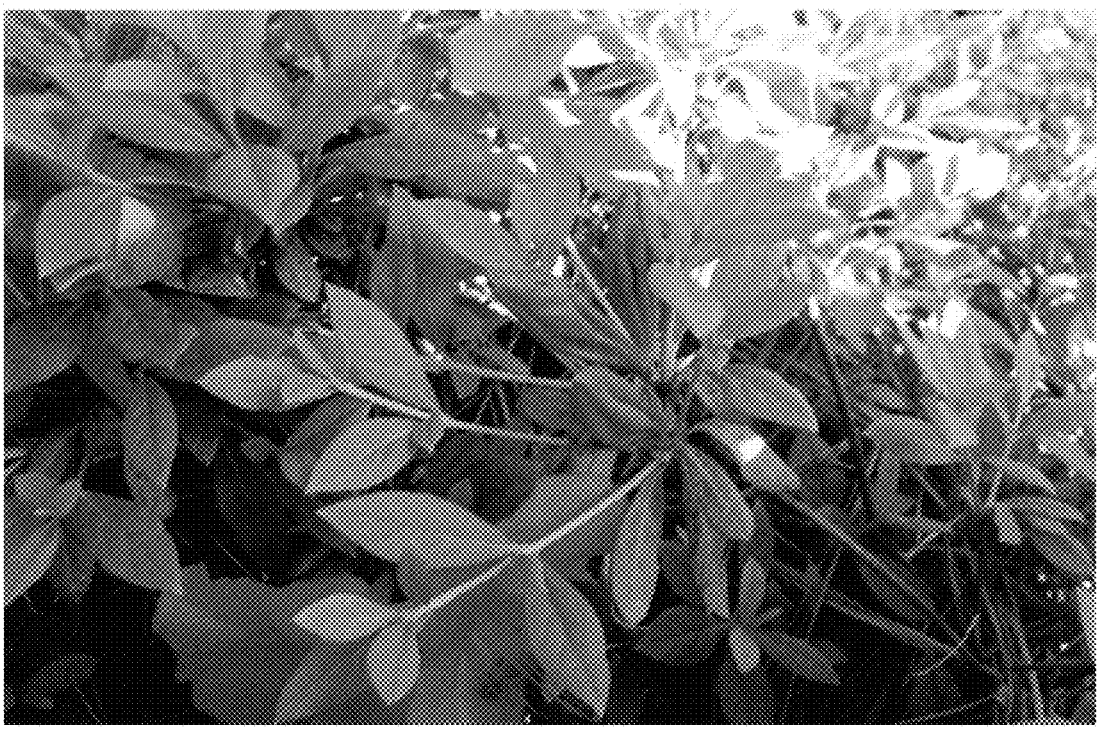
Figure 4:
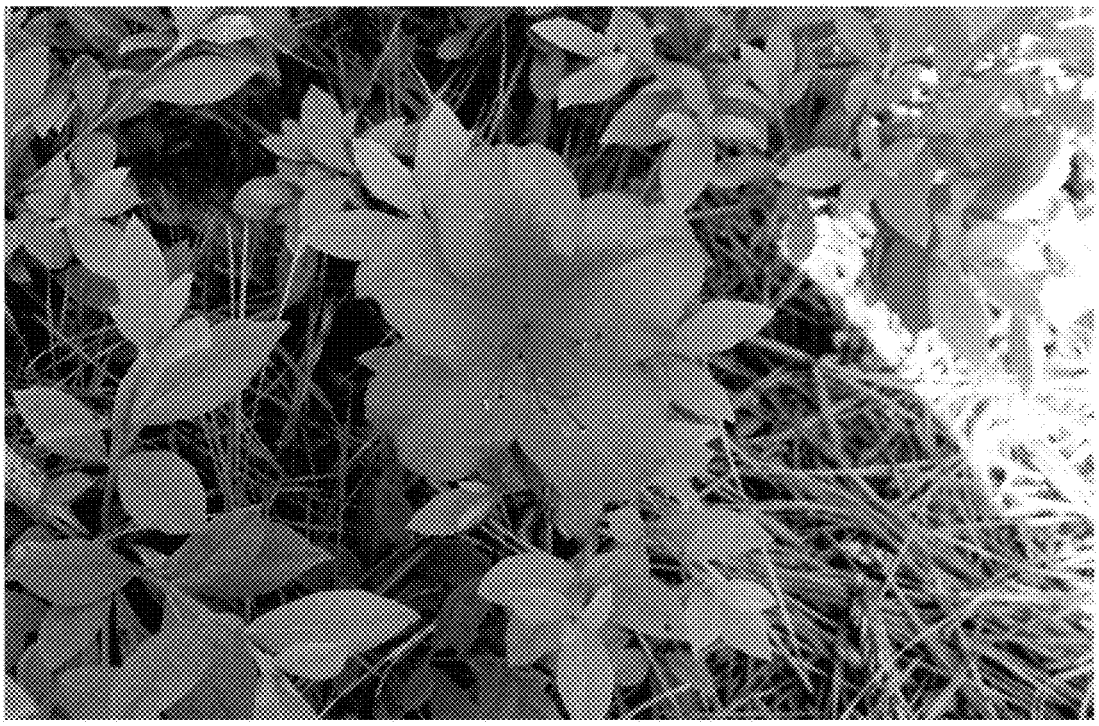

FIG. 1 shows a close-up of mature and immature foliage.
FIG. 2 shows mature foliage and growth habit.
FIG. 3 shows a close-up of the flower buds and new growth.
FIG. 4 shows a close-up of the flower size, form, and color.

DETAILED BOTANICAL DESCRIPTION OF THE NEW PLANT

The following is a detailed description of the new azalea variety based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Denomination*.—'MNIHAR027'.

Parentage:

*Female parent*.—The azalea plant named 'N1XE' (unpatented).

*Male parent*.—The azalea plant 'September Morn' (unpatented).

Plant:

*Form*.—Low growing, spreading.

*Texture*.—Medium.

*Height* (*at maturity*).—60.96 cm to 76.2 cm.

*Width* (*at maturity*).—213.36 cm to 243.84 cm.

*Growth habit*.—Freely branching, low growing, and spreading

*Growth rate*.—Moderate growth rate under normal fertilization and moisture conditions. In a period of 5 years from a rooted cutting the plant reaches a height of 50.8 cm and a spread of 86.36 cm. The growth rate averages about 13.7 cm per year; the plant reaches a height of 60.96 cm to 76.2 cm at maturity while maintaining a low growing, spreading growth habit due to the abundant deliquescent branch development.

*Spring growth*.—The date of initial spring growth is March 26, followed by continuous growth through fall.

*Life cycle*.—Perennial evergreen.

Leaves:

*Arrangement*.—Alternate, simple.

*Shape*.—Obovate.

*Apex*.—Mucronate.

*Base*.—Acute.

*Margin*.—Entire.

*Length*.—3.5 cm.

*Width*.—1.3 cm.

*Venation pattern*.—Pinnate; the mid-veins and laterals are impressed on the upper surface and are prominent on the lower surface. Color (both upper and lower surfaces): RHS 145A (yellow-green).

*Immature leaf*.—Upper surface: Color: Matte, RHS 144B (yellow-green). Pubescence: Strigose and scabrous, mainly along midvein and margins. Color: RHS 155C (white). Lower surface: Color: Matte, RHS 146C (yellow-green). Pubescence: Strigose. Color: RHS 155C (white).

*Mature leaf*.—Upper surface: Color: Matte, RHS 147A (yellow-green). Pubescence: Strigose. Color: Mostly RHS 155C (white). Lower surface: Color: Matte, RHS 147B (yellow-green). Pubescence: Strigose. Color: RHS 164D (greyed-orange).

*Petiole*.—Length: 0.5 cm. Diameter: 0.2 cm by 0.15 cm. Pubescence: Strigose. Length: 0.2 cm. Color: Immature: RHS N155A (white) and RHS 159A (orange-white). Mature: RHS 166A (greyed-orange). Color: Immature: RHS 145A (yellow-green). Mature: RHS 144B (yellow-green).

Stems:

*Form*.—Branched at terminal buds with stems from auxiliary buds at leaf nodes.

*Young stems* (*actively growing, less than one year old*) .—Color: RHS 144A (yellow-green). Pubescence: Strigose. Pubescence color: Begins RHS N155A (white) and RHS 159A (orange-white) maturing to RHS 164A (greyed-orange). Length of fully elongated flush: 9.0 cm on average. Diameter: 0.2 cm.

*Mature stems* (*one year old and older*).—Color: RHS 199B (grey-brown), RHS N199B (grey-brown), and RHS 200A (brown). Pubescence: Strigose, the quantity decreases with age. Color: RHS 166A (greyed-orange). Length: 14.5 cm on average for full year's growth. Diameter: 0.3 cm in second year. Pith: Solid and uniform. Internode length: Average 1.3 cm on actively growing vegetative stems.

Flower buds:

*Arrangement and form* (*terminal end*).—Borne in groups of two or three, sheathed by one to three modified leaf bracts. Bract length: Average 2.5 cm. Bract Width: 0.4 cm. Bract Color: RHS 147A (yellow-green).

*Shape*.—Ovate.

*Apex*.—Acute.

*Base*.—Rounded.

*Length* (*at tight bud*).—0.95 cm.

*Diameter* (*at tight bud*).—0.6 cm.

*Scales*.—Color: Immature: RHS 145A (yellow-green). Mature: RHS 144A (yellow-green). Length: 1.3 cm. Diameter: 0.7 cm. Texture: Matte; strigose pubescence. Pubescence color: RHS 155C (white).

*Pedicel*.—Length: 0.8 cm. Diameter: 0.2 cm. Texture: Pubescent, strigose pubescence. Pubescence color: RHS N155D (white). Color: RHS 45A (red) and RHS 145A (yellow-green).

Calyx:

*Diameter*.—0.4 cm from sepal apex to sepal apex.

*Texture*.—Pubescent, strigose. Pubescence color: RHS 155D (white).

*Color*.—RHS 145A (yellow-green).

*Sepals*.—Length: 0.2 cm. Diameter: 0.2 cm. Quantity: 4 or 5.

Flowers:

*Type*.—Perfect, single flowers.

*Shape*.—Open funnel-shaped.

*Flowering habit and period*.—Borne on the current season's growth; two weeks beginning in mid April in Dearing, Ga.; flowering resumes late July and continues until frost which can be as late as November or December.

*Lastingness of flowers on the plant*.—3 to 5 days in the sun; 3 to 6 days in the shade.

*Fragrance*.—Absent.

*Persistance*.—Self-cleaning.

*Diameter*.—8.0 cm.

*Depth*.—3.8 cm.

*Petals*.—Quantity per flower and arrangement: Six imbricate petals that are fused at the base and remain fused up to 2.5 cm from the base. Shape: Obovate. Apex: Rounded. Base: Fused. Margin: Entire. Texture (Both upper and lower surfaces): Glabrous. Length (Petals without spots): 5.0 cm. Length (Petals with spots): 5.5 cm. Width (Petals without spots): 3.0 cm. Width (Petals with spots): 3.6 cm. Color: Upper surface: RHS 47A (red); spots on the upper surface of the petal are RHS 53A (red). Lower surface: RHS 47A (red) and RHS 44D (red); spots on the lower surface of the petal are not visible.

Reproductive parts:

*Pistil*.—Quantity and form: Single, non-petaloid. Length: 5.5 cm. Diameter: 0.05 cm.

*Stigma*.—Color: RHS 187C (greyed-purple). Diameter: 0.1 cm.

*Style color*.—RHS 53A (red).

*Ovary*.—Tomentose pubescence; RHS N155A (white) with 5 locules.

*Ovary color*.—RHS 143A (green).

*Stamens*.—Quantity: 8 to 10 per flower; non-petaloid. Length: Average 5.0 cm. Width: Average 0.03 cm. Color: RHS 46B (red).

*Anther*.—Length: 0.2 cm. Width: 0.1 cm. Color: RHS 187A (greyed-purple). Pollen: Abundant. Color: RHS 155D (white).

Fruit and seed: Observed.

*Maturity*.—The capsule matures in about 6 months in Dearing, Ga. and the fruit set is low and contains about 100 to 200 non-winged seeds.

*Capsule*.—Length: 0.6 cm. Width: 0.47 cm. Color: RHS 146B (yellow-green).

CULTURE

'MNIHAR027' grows well in a wide range of conditions and tolerates sun to shade. 'MNIHAR027' prefers moist, well-drained soil that is rich in organic matter and responds well to mulching and medium applications of fertilizer. 'MNIHAR027' does best in soil with a pH of 5.0 to 5.5 and is propagated with semi-hardwood cuttings in late spring through the summer. 'MNIHAR027' roots in five to six weeks with a high percentage of rooting (80% plus). Tissue culture is also an effective means of propagation of 'MNIHAR027'.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR027' is compared to the variety 'N1' (unpatented), the male parent 'September Morn' (unpat-en-ted), and the commercial variety 'Conleb' (U.S. Plant Pat. No. 10,851).

TABLE 1

| Characteristic | 'MNIHAR027' | 'N1' | 'September Morn' | 'Conleb' |
|---|---|---|---|---|
| Plant Height (Mature) | 60.96 cm to 76.2 cm | N/A | 76.2 cm | 121.92 cm to 152.4 cm |
| Flower Diameter | 6.3 cm | 8.89 cm | 5.08 cm to 6.35 cm | 6.5 cm |
| Flower Form | Single | Single | Single | Single to semi-double |
| Flower Color | Red | Red | Red | Red |
| Bloom Period | Mid April and late July until frost | Spring and Fall | Early April | April and late July until frost |
| Hardy Zone | 6 | N/A | 5 | 7 |
| Stamen Number | 9 | N/A | 5 | 0 to 9 |
| Stamen Type | Non-petaloid | Non-petaloid | Non-petaloid | Petaloid and non-petaloid |

Additionally, when 'MNIHAR027' is compared to the commercial variety 'Roblen' (U.S. Plant Pat. No. 16,248), 'MNIHAR027' has a low growing, spreading growth habit with a height of 50.8 cm and a spread of 86.36 cm in 5 years, while 'Roblen' has a height of 91.44 cm and a spread of 60.96 cm in six years. Also, 'MNIHAR027' has single flowers colored RHS 47A (red), while 'Roblen' has single to semi-double flowers colored RHS 44C (red).

I claim:

1. A new variety of azalea plant named 'MNIHAR027' as herein shown and described.

* * * * *